United States Patent [19]

Samuelsson et al.

[11] 4,041,066

[45] Aug. 9, 1977

[54] 4,5-CIS-DIDEHYDRO-PGE₁ COMPOUNDS

[75] Inventors: Bengt Samuelsson, Stockholm, Sweden; Barney J. Magerlein, Portage, Mich.

[73] Assignee: The Upjohn Company, Kalamazoo, Mich.

[21] Appl. No.: 611,804

[22] Filed: Sept. 9, 1975

Related U.S. Application Data

[60] Division of Ser. No. 440,628, Feb. 7, 1974, Pat. No. 3,954,835, which is a continuation of Ser. No. 248,005, April 27, 1972, abandoned.

[51] Int. Cl.² .......................................... C07C 177/00
[52] U.S. Cl. ...................... 260/468 D; 260/488 R; 260/514 D
[58] Field of Search ..................... 260/468 D, 514 D

[56] References Cited

U.S. PATENT DOCUMENTS 3,816,393   7/1974   Hayashi et al. ..................... 260/209

OTHER PUBLICATIONS

Van Dorp, Annals of the N.Y. Academy of Sciences, 180, pp. 181–186, (1971).

Primary Examiner—Robert Gerstl
Attorney, Agent, or Firm—Morris L. Nielsen

[57] ABSTRACT

This invention is a group of 4,5-didehydro and 4,5,17,18-tetrahydro PG₁ (prostaglandin-type) compounds, and processes for making them. These compounds are useful for a variety of pharmacological purposes, including anti-ulcer, inhibition of platelet aggregation, increase of nasal patency, labor inducement at term, and wound healing.

6 Claims, No Drawings

4,5-CIS-DIDEHYDRO-PGE₁ COMPOUNDS

CROSS REFERENCE TO RELATED APPLICATIONS

This is a division of copending application Ser. No. 440,628, filed Feb. 7, 1974, now issued as U.S. Pat. No. 3,954,835, which was a continuation of copending application Ser. No. 248,005, filed Apr. 27, 1972, since abandoned.

BACKGROUND OF THE INVENTION

This invention relates to novel compositions of matter, to novel methods for producing those, and to novel chemical intermediates useful in those process. Particularly, this invention relates to certain novel analogs of some of the known prostaglandins in which a cis carbon-carbon double bond links C-4 and C-5 in the carboxy-terminated chain.

The essential material for this application, including the background of the invention, the disclosure of the invention, and the description of the preferred embodiments, including Preparations and Examples, is incorporated by reference from U.S. Pat. No. 3,954,835, Ser. No. 440,628, columns 1–30, inclusive, under the provisions of M.P.E.P. 608.01(p).

4,5-Didehydro-PGE₁ is mentioned in the prior art (see van Dorp, Annals N.Y. Acad. Sci. vol. 180, page 181, esp. pp. 184–185, 1971).

SUMMARY OF THE INVENTION

It is a purpose of this invention to provide novel prostaglandin analogs in which a cis carbon-carbon double bond links C-4 and C-5 in the carboxy-terminated chain. It is a further purpose to provide esters, lower alkanoates, and pharmacologically acceptable salts of said analogs. It is a further purpose to provide a novel process for preparing said acids and esters. It is still a further purpose to provide novel intermediates useful in said process.

The presently described acids and esters of the 4,5-unsaturated prostaglandin analogs include compounds of the following formulas, and also the racemic compounds of each respective formula and the mirror image thereof:

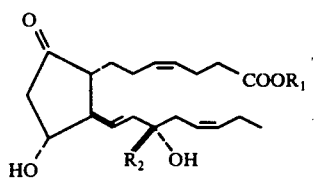

XII

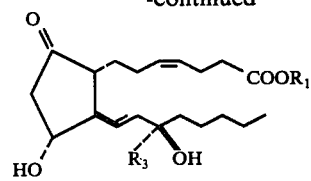

XVI

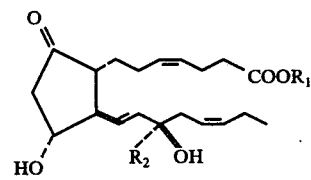

XX

In formulas XII, XVI, and XX, $R_1$ is hydrogen, alkyl of one to 12 carbon atoms, inclusive, cycloalkyl of 3 to 10 carbon atoms, inclusive, aralkyl of 7 to 12 carbon atoms, inclusive, phenyl, phenyl substituted with one to 3 chloro or alkyl of one to 4 carbon atoms, inclusive; $R_2$ is hydrogen, methyl, or ethyl; and $R_3$ is methyl or ethyl.

Formula XII represents 4,5-cis-17,18-cis-tetradehydro-PGE₁ when $R_1$ and $R_2$ are hydrogen.

We claim:

1. An optically active compound of the formula

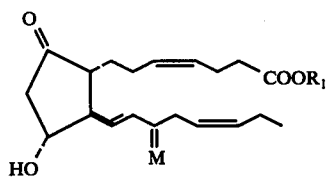

or a racemic compound of that formula and the mirror image thereof, wherein M is

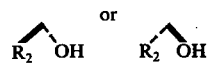

wherein $R_2$ is hydrogen, methyl, or ethyl; wherein $R_1$ is hydrogen, alkyl of one to 12 carbon atoms, inclusive, cycloalkyl of 3 to 10 carbon atoms, inclusive, aralkyl of 7 to 12 carbon atoms, inclusive, phenyl, or phenyl substituted with one, 2, or 3 chloro or alkyl of one to 4 carbon atoms, inclusive; including the lower alkanoates thereof, and the pharmacologically acceptable salts thereof when $R_1$ is hydrogen.

2. 4,5-cis-17,18-cis-Tetradehydro-PGE₁, a compound according to claim 1 wherein M is

and $R_1$ is hydrogen.

3. 4,5-cis-17,18-cis-Tetradehydro-PGE₁, methyl ester, a compound according to claim 1.

4. 15(R)-15-Methyl-4,5-cis-didehydro-PGE₁, and the methyl ester thereof.

5. 15(R)-15-Methyl-4,5-cis-didehydro-PGE₁, a compound according to claim 4.

6. 15(R)-15-Methyl-4,5-cis-didehydro-PGE₁, methyl ester, a compound according to claim 4.

* * * * *